United States Patent

Matsuzawa et al.

[11] Patent Number: 6,114,525
[45] Date of Patent: Sep. 5, 2000

[54] METHOD FOR PURIFYING NUCLEIC ACID DERIVATIVES

[75] Inventors: Toshihiro Matsuzawa; Tohru Nishiwaki, both of Kanagawa-ken; Seiichi Nishi, Mie-ken; Masanobu Yatagai, Kanagawa-ken, all of Japan

[73] Assignee: Ajinomoto Co., Inc., Tokyo, Japan

[21] Appl. No.: 09/113,509

[22] Filed: Jul. 10, 1998

[30] Foreign Application Priority Data

Jul. 10, 1997 [JP] Japan ................................. 9-185343

[51] Int. Cl.[7] ................................................ C07D 473/18
[52] U.S. Cl. ............................................................ 544/276
[58] Field of Search ............................................. 544/276

[56] References Cited

U.S. PATENT DOCUMENTS 5,874,578 2/1999 Singh ........................................ 544/276

FOREIGN PATENT DOCUMENTS

| 0 184 473 | 6/1986 | European Pat. Off. . |
| 0 502 690 | 9/1992 | European Pat. Off. . |
| 0 675 123 | 10/1995 | European Pat. Off. . |
| WO 97/18211 | 5/1997 | WIPO . |

OTHER PUBLICATIONS

J.C. Martin, et al., Journal of Medical Chemistry, vol. 26, No. 5, pp. 759–761, "9–[(1,3–Dihydroxy–2–Propoxy)-Methyl]Guanine: A New Potent and Selective Antiherpes Agent", May, 1983.

Primary Examiner—Mark L. Berch
Attorney, Agent, or Firm—Oblon, Spivak, McClelland, Maier & Neustadt, P.C.

[57] ABSTRACT

A pure (−)-9-[1'S, 2'R-bis(hydroxymethyl)cyclopropan-1'-yl]methylguanine is prepared by:

suspending or dissolving a mixture comprising (−)-9-[1'S, 2'R-bis(hydroxymethyl)cyclopropan-1'-yl]methylguanine and (7-[1'S,2'R-bis(hydroxymethyl)cyclopropan-1'-yl]methylguanine in an alcohol or a hydrous alcohol, reacting the resulting suspension or solution with an alkali metal hydroxide or alkoxide, and selectively precipitating crystals of nucleic acid derivatives of formula (I)

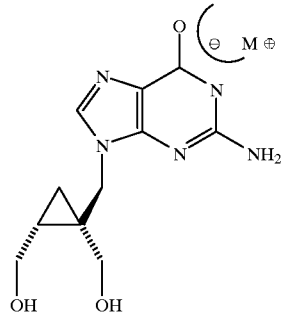

(I)

wherein M represents an alkali metal.

11 Claims, No Drawings

METHOD FOR PURIFYING NUCLEIC ACID DERIVATIVES

BACKGROUND OF THE INVENTION

1. Field of the Invention

The present invention relates to a process of producing nucleic acid derivatives which are useful as an antiviral agent. More specifically, the present invention relates to a method for purifying nucleic acid derivatives obtained by alkylating a purine base, and intermediates in the purification thereof.

2. Description of the Background (−)-9-[1'S,2'R-Bis(hydroxymethyl)cyclopropan-1'-yl]methylguanine represented by formula (II)

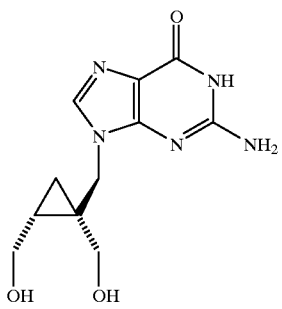

(II)

is known to have a high antiviral activity (Japanese Patent Laid-Open No. 78,357/1993).

The above-mentioned compound is produced by a process in which a protected purine base is alkylated as described in Japanese Patent Laid-Open Nos. 80,670/1994 and 316,155/1995. This alkylation occurs in both the 7- and 9-positions of the purine ring. In order to obtain a desired 9-substituted compound of the present invention, the 7-substituted compound and the unreacted purine base have had to be separated chromatographically.

SUMMARY OF THE INVENTION

Accordingly, one object of the present invention is to provide an industrial process for producing the compound of formula (II) simply without the necessity of having to employ an intricate procedure such as chromatography to separate the compound.

Briefly, this object and other objects of the present invention as hereinafter will become more readily apparent can be attained in a method of purification which comprises suspending or dissolving a mixture of (−)-9-[1'S,2'R-bis(hydroxymethyl)cyclopropan-1'-yl]methylguanine and 7-[1'S, 2'R-bis(hydroxymethyl)cyclopropan-1'-yl]methylguanine in an alcohol or a hydrous alcohol, reacting the suspension or the solution with an alkali metal hydroxide or alkoxide, and selectively precipitating crystals of the nucleic acid derivative represented by formula (I)

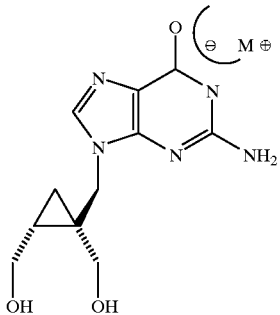

(I)

wherein M represents an alkali metal.

DETAILED DESCRIPTION OF THE PREFERRED EMBODIMENTS

The present inventors have conducted an investigation to solve the problems of the complicated separation and isolation of the 9-substituted isomer from the 7-substituted isomer, and have found that the desired 9-substituted compound of formula (I) can be obtained in high purity with good efficiency by reacting 2-amino-6-chloropurine with a compound obtained by substituting the hydroxyl group of (1S,5R)-3-oxa-2-oxobicyclo[3.1.0]hexane-1-methanol with a leaving group, suspending or dissolving the resulting mixture of desired (−)-9-[1'S,2'R-bis(hydroxymethyl)cyclopropan-1'yl]methylguanine and by-product 7-[1'S,2'R-bis(hydroxymethyl)cyclopropan-1'-yl]methylguanine in an alcohol or a hydrous alcohol, adding thereto an alkali metal hydroxide, an aqueous solution of an alkali metal hydroxide, an alcohol solution of an alkali metal hydroxide, an alkali metal alkoxide or an alcohol solution of an alkali metal alkoxide, then cooling the reaction mixture, and isolating crystals which precipitate.

(−)-9-[1'S,2'R-Bis(hydroxymethyl)cyclopropan-1'-yl]methylguanine represented by formula (II) which is a starting material of the synthesis of the invention, can be prepared by the process described in Japanese Patent Laid-Open Nos. 80,670/1994 and 316,155/1995. For example, 2-amino-6-chloropurine is reacted with 1-bromomethyl-4,4-diphenyl-3,5-dioxabicyclo[5,1,0]octane in N,N-dimethylformamide solvent in the presence of potassium carbonate, and 2-amino-6-chloro-9-(4', 4'-diphenyl-3',5'-dioxabicyclo[5,1,0]octyl-1'-) methylpurine obtained is hydrolyzed in formic acid by heating to form the desired (−)-9-[1'S,2'R-bis(hydroxymethyl) cyclopropan-1'-yl]methylguanine as an aqueous solution. This solution is concentrated to dryness, then dissolved in an aqueous sodium hydroxide solution, washed with ethyl acetate, and neutralized with hydrochloric acid, thereby obtaining the desired (−)-9-[1'S,2'R-bis(hydroxymethyl) cyclopropan-1'-yl]methylguanine as a crystalline substance.

Alternatively, 2-amino-6-chloropurine is reacted with (3-oxa-2-oxobicyclo[3,1,0]hexan-1-yl)methylmethanesulfonate in N,N-dimethylformamide in the presence of potassium carbonate. 2-Amino-6-chloro-9-(3'-oxa-2'-oxobicyclo [3,1,0] hexan-1'-yl)methylpurine obtained is hydrolyzed with hydrochloric acid, and neutralized to give 9-(3'-oxa-2'-oxobicyclo[3,1,0]hexan-1'-yl]methylguanine as a crystalline substance. This compound is reduced with sodium borohydride in ethanol solvent, and treated with an acid. The thus-treated substance is subjected to substitution with a sodium hydroxide aqueous solution, and neutralized to obtain the desired (−)-9-[1'S,2'R-bis(hydroxymethyl) cyclopropan-1'-yl]methylguanine as a crystalline substance.

The crystals obtained by these methods contain, as mentioned above, are the desired (−)-9-[1'S,2'R-bis(hydroxymethyl) cyclopropan-1'-yl']methylguanine of formula (II), 7-[1'S,2'R-bis(hydroxymethyl)cyclopropan-1'-yl] methylguanine, which has formula (III) in which the 7-position of guanine is substituted, and guanine.

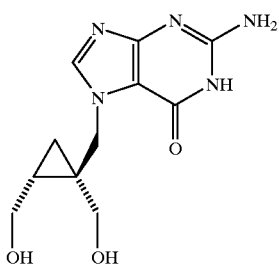

(III)

The desired compound of formula (I) of the present invention can be purified and produced from the mixture obtained by the above-described methods in the following manner.

First, the starting compound (II) containing impurities such as 7-[1'S,2'R-bis(hydroxymethyl)cyclopropan-1'-yl] methylguanine and the like is suspended in an alcohol solvent such as methanol, ethanol or 2-propanol or in an alcohol solvent containing water at a volume ratio of from 0–50%. At this time, the concentration of the compound ranges preferably from 2–15% (w/w). Then, an alkali metal hydroxide, an aqueous solution of an alkali metal hydroxide, an alcohol solution of an alkali metal hydroxide, an alkali metal alkoxide or an alcohol solution of an alkali metal alkoxide in an amount of from 1–5 equivalents based on compound (II) is added to this suspension. The reaction is conducted at from 0° C. to the solvent reflux temperature for from 0.5–50 hours. Subsequently, the reaction mixture is cooled to a temperature ranging from 0–30° C., preferably from 0–10° C., and aged for 0.5–50 hours, thereby obtaining the desired compound of formula (I) as a crystalline substance. This compound can easily be isolated by filtration.

Alternatively, the starting compound (II) is dissolved in an aqueous alkaline solution, which is an aqueous sodium hydroxide solution, an aqueous potassium hydroxide solution or an aqueous lithium hydroxide solution, and an alcohol solvent such as methanol, ethanol or 2-propanol is added thereto. The desired compound of formula (I) is precipitated by cooling the solution, and is recovered as a crystalline substance.

The compound of formula (I) of the present invention can also be represented by formula (II).

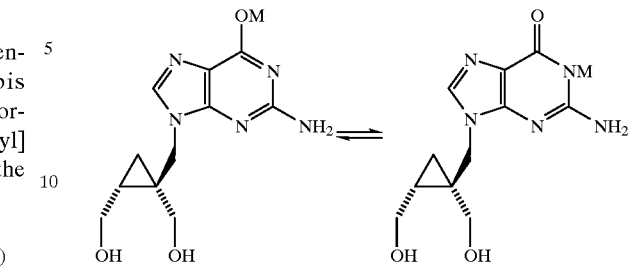

(I')

wherein M represents an alkali metal.

Suitable examples of the alkali metal as the cation of the salt compound prepared include sodium, potassium and lithium. Suitable examples of the alkali metal hydroxide include sodium hydroxide, potassium hydroxide and lithium hydroxide. Suitable examples of the alkali metal alkoxide include solid compounds such as sodium methylate, sodium ethylate, sodium tert-butylate, potassium methylate and potassium tert-butylate, and the corresponding alcohol solutions.

With respect to preferred combinations, one technique is to add a methanol solution of sodium methylate to a methanol suspension. The reason this technique is preferred is that the reagent is easily obtainable at a low cost and also easy to handle. Moreover, the crystallinity of the product obtained is good, along with having a high purity and a high yield.

Crystals of the compound of formula (I) prepared by the process of the present invention can be obtained in high purity. The amounts of isomer impurities and guanine, which are hard to remove, can be reduced to appreciable levels.

The process of the present invention enables the artisan to avoid having to employ the intricate and economically disadvantageous procedure of purification with a silica gel column which is normally used to remove the above-mentioned impurities. Further, the compound of formula (I) can easily be converted to the compound of formula (II) by hydrolysis.

Having generally described this invention, a further understanding can be obtained by reference to certain specific examples which are provided herein for purposes of illustration only and are not intended to be limiting unless otherwise specified.

EXAMPLE 1

Production of (−)-9-[1'S,2'R-bis(hydroxymethyl) cyclopropan-1'-yl]methylguanine sodium salt:

<Process 1>

(−)-9-[1'S,2'R-Bis(hydroxymethyl)cyclopropan-1'-yl] methylguanine was prepared by the process described in Japanese Patent Laid-Open No. 80,670/1994 without conducting purification by use of silica gel column chromatography, thereby obtaining 44.8 g of a crude product. This product contained 63.6% of the desired product and 21.9% of the 7-position isomer.

This mixture was dissolved in 40 ml of an aqueous 4.5-N sodium hydroxide solution, and 730 ml of methanol were added thereto with stirring at room temperature. The reaction solution was cooled for 2 hours with stirring in an ice bath. The crystals which precipitated were filtered, and washed with a small amount of hydrous methanol. The resulting crystals were dried at 70° C. under reduced pressure for 3 hours to give 22.3 g of the above 9-substituted compound. In the product, the content of the above 9-substituted compound reached 88.9% (yield 64.2%), and the content of the 7-position isomer decreased to 0.25%.

<Process 2>

Unpurified (−)-9-[1'S,2'R-bis(hydroxymethyl) cyclopropan-1'-yl]methylguanine was prepared by the process described in Japanese Patent Laid-Open No. 316,155/1995, thereby obtaining 39.9 g of a crude product. The contents of the desired product, the 7-position isomer and guanine were 67.9%, 9.9% and 3.8% respectively. This mixture was suspended in methanol, and the suspension was stirred at 45° C. with the addition of a methanol solution of sodium methoxide. After the mixture was stirred for 1 hour, the reaction solution was cooled to 10° C., and the crystals, which had precipitated, were filtered, and washed with a small amount of methanol. The resulting crystals were dried at 50° C. under reduced pressure, thereby obtaining 28 g of the above-mentioned compound as a single substance (content 94.4%, yield 90.2%).

White crystal $^1$H-NMR (300 MHz, CD$_3$OD) δ: 0.46 (t, J=5.5 Hz, 1H), 0.99 (dd, J=8.8, 5.2 Hz, 1H), 1.36 (tt, J=8.8, 6.2 Hz, 1H), 3.35 (d, J=12.6 Hz, 1H), 3.47 (dd, J=11.9, 8.8 Hz, 1H), 3.58 (d, J=12.6 Hz, 1H), 3.75 (dd, J=11.9, 6.5 Hz, 1H), 3.83 (d, J=14.4 Hz, 1H), 4.23 (d, J=14.9 Hz, 1H), 7.60 (s, 1H).

$^{13}$C-NMR (75 MHz, CD$_3$OD) δ: 14.9, 25.6, 28.7, 49.3, 62.5, 62.8, 119.0, 138.0, 153.1, 162.1, 169.1.

Mass spectrum (FAB) 288 (MH$^+$);

Melting point 220–230° C.

EXAMPLE 2

Production of (−)-9-[1'S,2'R-bis(hydroxymethyl) cyclopropan-1'-yl]methylguanine potassium salt:

A 0.5 g amount of unpurified (−)-9-[1'S,2'R-bis (hydroxymethyl)cyclopropan-1'-yl]methylguanine, which is a mixture of the desired 9-substituted isomer, the 7-position isomer and guanine in amounts of 85.7%, 5.3% and 3.2% respectively, obtained by the process described in Japanese Patent Laid-Open No. 316,155/1995, was suspended in 3 ml of methanol, and a potassium hydroxide methanol solution (0.23 g/3 ml) was added thereto with stirring. After the impure substance had dissolved, the crystals which precipitated were filtered, and washed with a small amount of methanol. The resulting crystals were dried at 45° C. under reduced pressure for 5 hours, thereby obtaining 0.35 g (yield 61.2%) of the above 9-substituted compound. Upon analysis, it was found that the content of the 9-substituted isomer in the crystalline substance was 98.5%, while the contents of the 7-position isomer and guanine were 0.7% and 0.3% respectively.

White crystal $^1$H-NMR (300 MHz, CD$_3$OD) δ: 0.46 (t, J=5.4 Hz, 1H), 0.99 (dd, J=8.6, 5.2 Hz, 1H), 1.35 (tt, J=8.6, 6.1 Hz, 1H), 3.34 (d, J=12.4 Hz, 1H), 3.46 (dd, J=11.8, 8.8 Hz, 1H), 3.58 (d, J=12.6 Hz, 1H), 3.76 (dd, J=11.9, 6.4 Hz, 1H), 3.83 (d, J=14.6 Hz, 1H), 4.23 (d, J=14.6 Hz, 1H), 7.60 (s, 1H).

$^{13}$C-NMR (75 MHz, CD$_3$OD) δ: 14.9, 25.6, 28.7, 49.3, 62.5, 62.7, 119.0, 138.0, 153.1, 162.1, 169.0.

Mass spectrum (ESI) 304 (MH$^+$);

Melting point 186–188° C.

EXAMPLE 3

Production of (−)-9-1'S,2'R-bis(hydroxymethyl) cyclopropan-1'-yl]methylguanine lithium salt:

A 0.5 g amount of unpurified (−)-9-[1'S,2'R-bis (hydroxymethyl)cyclopropan-1'-yl]methylguanine, which was a mixture of the 9-substituted isomer, the 7-position isomer and guanine in amounts of 85.7%, 5.3% and 3.2% respectively), obtained by the process described in Japanese Patent Laid-Open No. 316, 155/1995, was suspended in 6 ml of methanol, and 0.18 g of lithium hydroxide monohydrate was added-thereto at room temperature with stirring. After the substance had dissolved, the crystals which precipitated were filtered, and washed with a small amount of methanol. The resulting crystals were dried at 45° C. under reduced pressure for 5 hours to give 0.48 g (yield 93.9%) of the above-mentioned compound. In the product, the content of the 9-substituted compound was 96.8%, and the contents of the 7-position isomer and guanine were 1.1% and 1.4% respectively.

<Process 2>

A 0.5 g amount of unpurified (−)-9-[1'S,2'R-bis (hydroxymethyl)cyclopropan-1'-yl]methylguanine, which was a mixture of the desired 9-substituted isomer, the 7-position isomer and guanine in amounts of 85.7%, 5.3% and 3.2% respectively, obtained by the process described in Japanese Patent Laid-Open 316,155/1995, was suspended in 7 ml of ethanol, and 0.18 g of lithium hydroxide monohydrate and 0.5 ml of water were added thereto at room temperature with stirring. The crystals which precipitated were filtered, and washed with a small amount of ethanol. The resulting crystals were dried at 45° C. under reduced pressure for 5 hours to give 0.5 g (yield 97.8%) of the above 9-substituted compound. In the product, the content of the 9-substituted compound was 98.8%, and the contents of the 7-position isomer and guanine were 0.6% and 0.3% respectively.

White crystal $^1$H-NMR (300 MHz, CD$_3$OD) δ: 0.48 (t, J=5.3 Hz, 1H), 1.02 (dd, J=8.7, 4.9 Hz, 1H), 1.37 (m, 1H), 3.35 (—CD$_3$OD—), 3.47 (dd, J=12.1, 8.7 Hz, 1H), 3.59 (d, J=12.5 Hz, 1H), 3.76 (dd, J=11.9, 6.5 Hz, 1H), 3.85 (d, J=14.6 Hz, 1H), 4.24 (d, J=14.3 Hz, 1H), 7.65 (s, 1H).

Mass spectrum (FAB) 272 (MH$^+$);

Melting point 257° C. (decomp.)

EXAMPLE 4

Hydrolysis of (−)-9-[1'S,2'R-bis(hydroxymethyl) cyclopropan-1'-yl]methylguanine sodium salt:

(−)-9-[1'S,2'R-bis(hydroxymethyl)cyclopropan-1'-yl] methylguanine sodium salt (21.7 g) prepared by "Process 2" of Example 1 was dissolved in 410 ml of water with stirring. 3-N hydrochloric acid was added thereto until the pH of the solution reached a neutral value. The resulting suspension was stirred at 30° C. for 2 hours. Subsequently, the crystals, which had precipitated, were filtered, and washed with a small amount of water. The washed crystals were dried overnight at 70° C. under reduced pressure to give 18.8 g (content 96.8%, yield 96.5%) of high-purity (−)-9-[1'S,2'R-bis(hydroxymethyl)cyclopropan-1'-yl]methylguanine. The properties thereof were completely consistent with those of the compound described in Japanese Patent Laid-Open No. 78,357/1993.

In accordance with the present invention, salts of nucleic acid derivatives having an antiviral activity can easily be produced with good efficiency, and the 7-position isomer and other impurities can effectively be separated from the desired 9-substituted isomer during its production.

The disclosure of Japanese priority application serial number 9-185343 filed Jul. 10, 1997 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent is:

1. A method of separation, which comprises:

suspending or dissolving a mixture comprising (−)-9-[1'S,2'R-bis(hydroxymethyl)cyclopropan-1'-yl]methylguanine and 7-[1'S,2'R-bis(hydroxymethyl)cyclopropan-1'-yl]methylguanine in an alcohol or aqueous alcohol;

reacting the resulting suspension or solution with an alkali metal hydroxide or alkoxide; and selectively precipitating crystals of nucleic acid derivatives having formula (I)

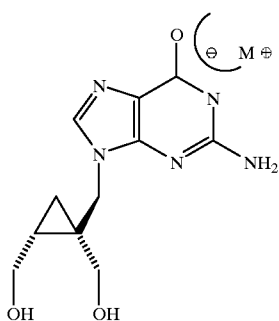

(I)

wherein M represents an alkali metal.

2. The method according to claim 1, wherein said aqueous alcohol solvent is a mixture of water in alcohol in an amount of up to 50 vol. % water.

3. The method of claim 1, wherein said reaction is conducted at a temperature of 0° C. to the reflux temperature of the solvent.

4. The method of claim 1, wherein said reaction solution is cooled to a temperature of 0–30° C., thereby precipitating the 9-substituted isomer.

5. The method of claim 1, wherein said alkali metal hydroxide is sodium, potassium or lithium hydroxide.

6. The method of claim 5, wherein the alkali metal hydroxide is sodium hydroxide.

7. The method of claim 1, wherein the alkali metal alkoxide is sodium or potassium alkoxide.

8. The method of claim 7, wherein the alkali metal alkoxide is sodium alkoxide.

9. The method of claim 7, wherein said alkoxide is sodium methylate, sodium ethylate, sodium t-butylate, potassium methylate or potassium t-butylate.

10. The method according to claim 1, wherein said alcohol solvent is methanol, ethanol or 2-propanol.

11. The method according to claim 2, wherein the concentration of said 7-[1'S,2'R-bis(hydroxymetlhyl)cyclopropan-1'-yl]methylguanine ranges from 2–15% (w/w).

* * * * *